US010390534B2

(12) United States Patent
Marrone et al.

(10) Patent No.: US 10,390,534 B2
(45) Date of Patent: Aug. 27, 2019

(54) COMPOSITIONS AND METHODS FOR MODULATING PLANT PARASITIC NEMATODES

(71) Applicant: Marrone Bio Innovations, Inc., Davis, CA (US)

(72) Inventors: Pamela Marrone, Davis, CA (US); Timothy B. Johnson, Davis, CA (US); Hai Su, Davis, CA (US); Lijuan Xing, Davis, CA (US); Phyllis Himmel, Davis, CA (US)

(73) Assignee: Marrone Bio Innovations, Inc., Davis, CA (US)

(*) Notice: Subject to any disclaimer, the term of this patent is extended or adjusted under 35 U.S.C. 154(b) by 518 days.

(21) Appl. No.: 15/296,386

(22) Filed: Oct. 18, 2016

(65) Prior Publication Data
US 2017/0086466 A1 Mar. 30, 2017

Related U.S. Application Data

(60) Division of application No. 14/581,880, filed on Dec. 23, 2014, now Pat. No. 9,526,252, which is a continuation of application No. 14/072,691, filed on Nov. 5, 2013, now Pat. No. 8,951,585, which is a continuation-in-part of application No. 13/280,311, filed on Oct. 24, 2011, now Pat. No. 8,715,754, said application No. 14/581,880 is a continuation of application No. 14/072,691, filed on Nov. 5, 2013, which is a continuation-in-part of application No. 13/843,971, filed on Mar. 15, 2013, now Pat. No. 8,822,193, which is a continuation-in-part of application No. 13/034,575, filed on Feb. 24, 2011, now Pat. No. 9,701,673, said application No. 14/581,880 is a continuation of application No. 14/072,691, filed on Nov. 5, 2013, now Pat. No. 8,951,585, which is a continuation-in-part of application No. PCT/US2013/030631, filed on Mar. 13, 2013.

(60) Provisional application No. 61/733,730, filed on Dec. 5, 2012, provisional application No. 61/609,937, filed on Mar. 13, 2012, provisional application No. 61/406,569, filed on Oct. 25, 2010, provisional application No. 61/406,541, filed on Oct. 25, 2010, provisional application No. 61/308,287, filed on Feb. 25, 2010.

(51) Int. Cl.
*A01N 63/00* (2006.01)
*A01N 63/02* (2006.01)
*C12N 1/20* (2006.01)
*C12P 1/04* (2006.01)

(52) U.S. Cl.
CPC ............ *A01N 63/00* (2013.01); *A01N 63/02* (2013.01); *C12N 1/20* (2013.01); *C12P 1/04* (2013.01)

(58) Field of Classification Search
None
See application file for complete search history.

(56) References Cited

U.S. PATENT DOCUMENTS

| 5,047,424 | A | 9/1991 | Puritch |
| 5,428,175 | A | 6/1995 | Hoshino |
| 6,077,860 | A | 6/2000 | Meunier |
| 6,103,228 | A | 8/2000 | Heins |
| 6,524,998 | B1 | 2/2003 | Kloepper |
| 7,037,494 | B2 | 5/2006 | Mattingly |
| 7,244,607 | B2 | 7/2007 | Martin |
| 8,691,219 | B2 | 4/2014 | Martin |
| 8,808,719 | B1 | 8/2014 | Flor-Weiler |
| 2003/0068304 | A1 | 4/2003 | Mattingly |
| 2005/0074431 | A1 | 4/2005 | Martin et al. |
| 2007/0172463 | A1 | 7/2007 | Martin |
| 2009/0111759 | A1 | 4/2009 | Pedersen |
| 2012/0100236 | A1 | 4/2012 | Asolkar |
| 2014/0199269 | A1 | 7/2014 | Asolkar |
| 2014/0227228 | A1 | 8/2014 | Asolkar |
| 2014/0303075 | A1 | 10/2014 | Asolkar |
| 2014/0322171 | A1 | 10/2014 | Flor-Weiler |

FOREIGN PATENT DOCUMENTS

| KR | 10-2007-088150 | 8/2007 |
| WO | 91/00012 A1 | 1/1991 |
| WO | 01/74161 A2 | 10/2001 |
| WO | 2011100424 A1 | 8/2011 |
| WO | 2011/110932 A1 | 9/2011 |
| WO | 2012140207 A2 | 10/2012 |
| WO | 2013/062977 A1 | 5/2013 |

OTHER PUBLICATIONS

Arena et al., "Tile Mechanism of Action of Averrnectins in Caenorhabditis Elegans:Correlation Between Activation of Glutamate-Sensitive Chloride Current, Membrane Binding and Biological Activity." Journal of Parasitology, 1995, vol. 31, No. 2, pp. 286-294.

(Continued)

*Primary Examiner* — Russell G Fiebig
(74) *Attorney, Agent, or Firm* — Chainey P. Singleton; Ying-Horng Liu

(57) ABSTRACT

Provided is a method for modulating soybean cyst nematode infestation of a plant comprising applying to the plant an effective amount of a composition comprising a *Chromobacterium*, *Burkholderia*, and/or *Flavobacterium* strain to modulate the soybean cyst nematode infestation. The composition may be applied directly to the seed or in a substrate for growing the plant, such as in the soil.

8 Claims, No Drawings

(56) References Cited

OTHER PUBLICATIONS

Asolkar et al., "Daryarnides A-C, Weakly Cytotoxic Polyketides from a Marine-Derived Actinomycete of the Genus Streptomyces Strain CNQ-OB5." J. Nat Prod, 2006, vol. 69, pp. 1756-1759.
Aspelin et al. "Pesticides Industry Sales and Usage, 1996 and 1997 Market Estimates." U.S E.PA Publication, 1999, 733-R-99-001.
Bakhetia et al., "RNA Intetference of Dual Oxidase in the Plant Nematode Meloidogyne Incognita." Molecular Plant-Microbe Interactions, 2005, vol. 18, pp. 1099-1106.
Balibar et al. "In Vitro Biosynthesis of Violacein from L-Tryptophan by the Enzymes VioA-E from Chromobacterium Violaceum." Biochemistry, 2006, vol. 45, pp. 15444-15457.
Brazilian National Genome Project Consortium, "The CompleteGenome Sequence of Chromobacterium Violaceum Reveals Remarkable andExploitable Bacterial Adaptability," Proc. Natl. Acad. Sci, 2003, vol. 100, No. 20, pp. 11660-11665.
Chalvet-Monfray et al., "Synergy BerNeen Deltamethrin and Prochloraz inBees: Modeling Approach." Environmental Toxicology and Chemistry, 1996, vol. 15, No. 4, pp. 525-534.
Chitwood. "Nematicides" in Encyclopedia of Agrochemicals, J. R. Plimmer (ed). New York, John Wiley & Sons. 3: 2003, pp. 1104-1115.
Chitwood. "Phytochemical Based Strategies for Nematode Control" "AnnualReview of Phytopathology 40: 221-249. 2002."
Colby. "Calculating Synergistic and Antagonistic Responses of Herbicide Combinations." Weeds, 1967, vol. 15, No. 1, pp. 20-22.
Cronin et al. "Inhibition of Egg Hatch of the Potato Cyst Nematode Globodera Rostochiensis by Chitinase-Producing Bacteria." European Journal of Plant Pathology, 1997, vol. 103, pp. 433-440.
Dong et al. "Microbial Control of Plant-Parasitic Nematodes: A Five-Party,Interaction." Plant Soil, 2006, vol. 288, pp. 31-45.
Duran et al. "Biosynthesis of a Trypanocide by Chrornobacteriurn Violaceurn." World Journal of Microbiology and Biotechnology, 1994, Vo. 10, pp. 686-690.
Duran et al. "Chromobacteriurn Violaceurn: A Review of Pharmacological and Industrial Perspectives." Critical Reviews in Microbiology, 2001, vol. 27, pp. 201-222.
Duran et al. "Potential Applications of Violacein: a Microbial Pigment." Medical Chemisrty Research, 2012, vol. 21, pp. 1524-1532.
Duran et al. "Violacein: Properties and Biological Activities." Biotechnol. Appl.Biochern, 2007, vol. 48, pp. 127-133.
Duran et al. "Chromobacterium violaceum and Its Important Metabolites-review." Folia Microbiol, 2010, vol. 55, No. 6, pp. 535-547. [Abstract].
Extended European Search Report dated Jun. 7, 2016.
Farenhorst et al. "Synergy in Efficacy of Fungal Entomopathogens andPerrnethrin Against West African Insecticide-Resistant Anopheles GambiaeMosquitoes." PLoS ONE, 2010, vol. 5, No. 8, pp. 1-10, e12081.
Faske et al. "Sensitivity of Meloidogyne Incognita and Rotylenchulus Reniformis toAbamectin." Journal of Nematology, 2006, vol. 38, pp. 240-244.
Gelman, Dale B. et al., "Novel Candidates for the Development of Biopesticides to Control Whitefly Pest." Journal of Insect Science, Jan. 1, 2008, vol. 8, No. 4, pp. 19-20.
Giannakou et al., "Factors affecting the efficacy of non-fumigant nematicides for controlling root-knot nematodes." Pest management Science, 2005, vol. 61, pp. 961-972.
Guerena, Martin. "Nematodes: alternative controls." A Publication of ATTRA—National Sustainable Agriculture (2006).
Hallmann et al., "Toxicity of Fungal Endophyte Secondary Metabolites to Plant Parasitic Nematodes and Soil-Borne Pathogens." European Journal of Plant Pathology, 1996, vol. 102, pp. 155-162.
Hasky-Gunther et al., "Resistance Against the Potato Cyst NematodeGlobodera Pallida Systemically Induced by the Rhizobacteria Agrobacterium Radiobacter (G12) and Bacillus Sphaericus (B43)." Fundamentals of Applied Nematology, 1998, vol. 21, pp. 511-517.

Hoshino et al., "Biosynthesis of Violacein: Origins of the Hydrogen, Nitrogen and Oxygen Atoms in the 2-Pyrrolidone Nucleus." Agricultural and Biological Chemistry, 1987, vol. 51, pp. 2733-2741.
Hummelbrunner et al., "Acute, Sublethal, Antifeedant, and Synergistic Effectsof Monoterpenoid Essential Oil Compounds on the Tobacco Cutworm, SpodopteraLitura (Lep., Noctuidae)" Journal of Agricultural and Food Chemistry, 2001, vol. 49, No. 2, pp. 715-720.
Hungria et al., "Genetic Characterization of Chromobacterium Isolates from Black Water Environments in the Brazilian Amazon." Letters in Applied Microbioology, 2005, vol. 41, pp. 17-23.
International Search Report and Written Opinion issued in PCT App. No. PCT/US2011/057541 dated Jun. 26, 2012.
Jaffee et al., "Susceptibility of Root-Knot and Cyst Nematodes to the Nematode-Trapping Fungi Monocrosporium Ellipsosporum and M. Cionopagum." Soil Biologyand Biochemistry, 1995, vol. 27, pp. 1083-1090.
Kampfer et a., "*Chromobacterium piscinae* sp. Nov. and *Chromobacteriumpseudoviolaceum* sp. Nov., from Environmental Samples." International Journal of Systematic and Evolutionary Microbiology, 2009, vol. 59, pp. 2486-2490.
Kerry. "Exploitation of the Nematophagous Fungal Verticillium Chlamydosporium Goddard for the Biological Control of Root-Knot Nematodes (*Meloidogyne* Spp.)," In Fungi as Biocontrol Agents: Progress. Problems and Potential. T. M. Butt, C.Jackson and N. Magan ( eds ). New York, CAB International, 2001, pp. 155-168.
Kirkegaard et al., "Biofurnigation Potential of *Brassicas*." Plant and Soil, 1998, vol. 201, pp. 71-89.
Koenning et al., "Survey of Crop Losses in Response to Phytoparasitic Nematodes in the United States for 1994." Supplement to the Journal of Nematology, 1999, 31(4S), pp. 587-618.
Kokalis-Burelle et al., "Alleochemicals as Biopesticides for management of Plant-Parasitic Nematodes." In Alleolochemicals: Biological Control of Plant Pathogens and Diseases. Inderfit and K. G. Mukerji (eds). Netherlands, Springer, 2006, pp. 15-29.
Krieg et al., "*Bacillus thuringiensis* var. *tenebrionis*: A New Pathotype Effective Against Larvae of Coleoptera." Z. Angew. Entomol, 1983, Vo. 96, pp. 500-508. (EnglishAbstract).
Martin, Phyllis et al., "Two New Bacterial Pathogens of Colorado Potato Beetle (*Coleoptera: Chrysomelidae*)." Journal of Economic Entomology, Jun. 2004, vol. 97, No. 3, pp. 774-780.
Martin et al., "A method to detect viable, pigmented insect pathogens from soil." Abstracts of the General Meeting of the American Society for Microbiology 103: Q-436, 2003.
Martin et al. "Characterization of *Chromobacterium* sp, a purple bacterium toxic to insects." Abstracts of the General Meeting of the American Society for Microbiology 103: Q-226, 2003.
Martin et al. "Survival of Chromobacterium Violaceurn, An Insect Pathogen UnderVarious Conditions." Abstracts of the General Meeting of the American Society for Microbiology, 2002, vol. 102, pp. 389-390.
Martin et al., "Toxicity of Chromobacterium Subtsugae to Southern Green Stink Bug (*Heteroptera: Pentatomidae*) and Corn Rootworm (*Coleoptera:Chrysomelidae*)" J. Econ. Entomol, 2007, vol. 100, No. 3, pp. 680-684.
Martin. "A Freeze-Dried Diet to Test Pathogens of Colorado Potato Beetle." Biological Control, 2004, vol. 29, No. 1, 109-114.
Martin et al., "Bacterial Strains Lethal to Colorado Potato Beetle Larvae." Abstracts of the General Ieeting of the American Society for Micorbiology 101 :603. 2001.
Martin et al., "*Chromobacterium subtsugae* sp. nov., a Betaproteobacterium Toxicto Colorado Potato Beetle and other Insect Pests." International Journal of Systematic and Evolutionary Microbiology, 2007, vol. 57, pp. 993-999.
McClean et al., "Quorum Sensing and Chromobacterium Violaceum: Exploitationof Violacein Production and Inhibition for the Detection of N-AcylhomoserineLactones." Microbiology, 1997, vol. 143, pp. 3703-3711.
Meyer et al., "Combinations of Biocontrol Agents for Management of Plant-Parasitic Nematodes and Soilborne Plant-Pathogenic Fungi." Journal of Nematology, 2002, vol. 34, pp. 1-8.
Oka et al., "Nematicidal Activity of Essential Oils and their Components Against the Root-Knot Nematode." Phytopathology, 2000, vol. 90, pp. 710-715.

(56) References Cited

OTHER PUBLICATIONS

Oostendorp et al., "In-vitro Interrelationships Between Rhizosphere Bacteria and Heterodera Schachtii." Reviews in Nematology, 1990, vol. 13, pp. 269-274.

Ouarles (ed.) "Directory of Least-Toxic Pest Control Products." The IPM Practitioner 26: •17. 2005.

Roubtsova et al. "Effect of Broccoli (*Brassica oleracea*) Tissue, Incorporated at Different Depths in a Soil Column, on Meloidogyne incognita." Journal of Nematology, 2007, vol. 39, pp. 111-117.

Ryan et al., "Divergent Pathways in the Biosynthesis of Bisindole Natural Products." Chemistry & Biology, 2009, vol. 6, No. 4, pp. 351-364.

Sanchez, et al., "Reevaluation of the Violacein Biosyntlletic Pathway and itsRelationship to Indolocarbazole Biosynthesis." ChemBioChem, 2006, vol. 7, No. 8, pp. 1231-1240.

Sasser et al., "A World Perspective on Nematology: The Role of the Society." Sasser et al. "A World Perspective on Nematology: The Role of the Society" Vistas on nematology: a commemoration of the twenty-fifth anniversary of the Society of Nematologists/edited by Joseph A. Veech and Donald W. Dickson. 1987, pp. 7-14.

Saxena et al., "Bacterial Biocontrol Agents and their Role in Plant DiseaseManagement." In Biocontrol Potential and its Exgloitation in SustainableAgriculture. vol. 1: Crog Diseases, Weeds. and Nematodes. R. R. Upadhaya,K. G. 1 Atlekerji and B. P. Chamola (eds). New York, Kluwer Academic PlenumPublishers. 2000, pp. 25-37.

Shapiro-I Lan et al. "Effects of Combining Microbial and Chemical Insecticides on Mortality of the Pecan Weevil (*Coleoptera: Curculionidae*)." JJournal of Economic Entomology, 2011, vol. 104, No. 1, pp. 14-20.

Siddiqui et al., "Neem Allelopathy and the Root Knot Nematode" "The IPMPractitioner 23:9-11. 2001."

Siddiqui et al., "Biological Control of Plant Parasitic Nematodes by Fungi: a Review." Bioresource Technology, 1996, vol. 58, pp. 229-239.

Siddiqui et al., "Role of Bacteria in the Management of Plant Parasitic Nematodes:a Review." Bioresource Technology, 1999, vol. 69, pp. 167-179.

Sikora et al. Biological control of plant-parasitic nematodes with plant-health promoting rhizobacteria. InPest management: biologically based technologies. Proceedings of Beltsville Symposium XVIII. Edited by RD Lumsden and JL Vaughn. American Chemical Society, Washington DC, 1993, pp. 166-172.

Smith, R.E., et al., "Nematocidal Activity of a Cyanogenic *Chromobacterium* Species." Bacteriological Proceedings, vol. 69, Jan. 1, 1969, G164, p. 43.

Terefe et al. "Effect of a Formulation of Bacillus Firmus on Root-Knot Nematode Meloidogyne Incognita Infestation and the Growth of Tomato Plants in the Greenhouse and Nursery." Journal of Invertebrate Pathology, 2009, vol. 100, pp. 94-99.

Thompson et al. "Spinosad—a Case Study: An Example from a Natural Products Discovery Programme." Pest Manaement Science, 2000, vol. 56, pp. 696-702.

Tian et al. "Bacteria used in the biological control of plant-parasitic nematodes: populations, mechanisms of action, and future prospects." FEMS Microbiology Ecology, 2007, vol. 61, pp. 197-213.

Website document entitled: "Factors affecting nematicide efficacy." (available at http://www3.syngenta.com/country/uk/SiteCollectionDocuments/Crops/nemathorin/5-factors-affecting-nematicide-efficacy.pdf). Downloaded from website May 15, 2015.

Whitehead. "Plant-Parasitic Nematodes, Their Importance and Control," In Plant Nematode Control. Wallingford, UK, CAB International. 1997, p. 1-12.

Wirth et al. "Synergy Between Toxins of *Bacillus thuringiensis* subsp. *Israelensisand Bacillus sphaericus*." Journal of Medical Entomology, 2004, vol. 41, No. 5, pp. 935-941.

Young et al., "*Chromobacterium aquaticum* sp. nov., isolated from spring water samples." International Journal of Systematic and Evolutionary Microbiology, 2008, vol. 58, pp. 877-880.

Zeck. "A Rating Scheme for Field Evaluation of Root-Knot Nematode Infestations." Pflanzenschutz-nachrichten. Bayer, 1971, vol. 24, No. 1, pp. 141-144.

COMPOSITIONS AND METHODS FOR MODULATING PLANT PARASITIC NEMATODES

CROSS REFERENCE TO RELATED APPLICATIONS

This patent application is a divisional application of U.S. patent application Ser. No. 14/581,880 filed on Dec. 23, 2014, which is (a) a continuation application of U.S. patent application Ser. No. 14/072,691 filed on Nov. 5, 2013, now U.S. Pat. No. 8,951,585, which is a continuation-in-part application of U.S. patent application Ser. No. 13/280,311 filed on Oct. 24, 2011, now U.S. Pat. No. 8,715,754, which is a non-provisional application of U.S. Provisional Patent Application No. 61/406,569 filed on Oct. 25, 2010; and (b) a continuation application of U.S. patent application Ser. No. 14/072,691 filed on Nov. 5, 2013, which is continuation-in-part patent application of U.S. patent application Ser. No. 13/843,971 filed on Mar. 15, 2013, now U.S. Pat. No. 8,822,193, which is continuation-in-part patent application of U.S. patent application Ser. No. 13/034,575 filed on Feb. 24, 2011, which is a non-provisional application of U.S. Provisional Patent Application No. 61/308,287 filed on Feb. 25, 2010 and U.S. Provisional Patent Application No. 61/406,541 filed on Oct. 25, 2010; and (c) a continuation patent application of U.S. patent application Ser. No. 14/072,691 filed on Nov. 5, 2013, which is continuation-in-part patent application of PCT Patent Application No. PCT/US13/30631 filed on Mar. 13, 2013, which is a PCT patent application of U.S. Provisional Patent Application No. 61/609,937 filed on Mar. 13, 2012 and U.S. Provisional Patent Application No. 61/733,730 filed on Dec. 5, 2012. All of the foregoing applications are hereby incorporated by reference in their entirety.

TECHNICAL FIELD

Disclosed herein are pesticidal *Chromobacterium*, *Burkholderia*, and *Flavobacterium* strains and compositions, as well as their methods of use for controlling plant parasitic nematodes, particularly, soybean cyst nematodes.

BACKGROUND

Nematodes are non-segmented, bilaterally symmetric, worm-like invertebrates that possess a body cavity and complete digestive system but lack respiratory and circulatory systems. Their body wall contains a multilayer cuticle, a hypodermis with four longitudinal cords, and internal musculature (Chitwood, D. J. (2003). Nematicides. Encyclopedia of Agrochemicals, vol 3. J. R. Plimmer. New York, John Wiley & Sons. 3: 1104-1115). Their body contents are mostly occupied by digestive and reproductive systems. Nematodes may be classified as either parasitic or free living. Parasitic nematodes may be classified by their hosts (e.g., plant parasites). Free living nematodes may be classified according to their feeding habits and include the following groups: (1) omnivores; (2) bacterial feeders; (3) fungal feeders and (4) predators.

Plant parasitic nematodes generally feed on underground parts of plants, such as roots, bulbs, and tubers as well as above ground parts of the plants, such as leaves and stems. Annual crop losses caused by plant-parasitic nematodes have been estimated to exceed US $100 billion (Koenning, S. R., Overstreet, C. et al. (1999). *Journal of Nematology* 31: 587-618). Examples of plant parasitic nematodes include but are not limited to nematodes belonging to *Meloidogyne* spp. (e.g., root-knot nematodes); *Pratylenchus* spp. (e.g., lesion nematodes); *Heterodera* spp. (e.g., cyst nematodes); *Globodera* spp. (cyst nematodes); *Ditylenchus* spp. (e.g., stem and bulb nematodes); *Tylenchulus* spp. (e.g., citrus nematodes), *Xiphinema* spp. (e.g., dagger nematodes); *Radopholus* spp. (burrowing nematodes); *Rotylenchulus* spp. (e.g. reniform nematodes); *Helicotylenchus* spp. and *Scutellonema* spp. (e.g. spiral nematodes); *Belonolaimus* spp. (e.g., sting nematodes); *Bursaphelenchus* spp. (e.g. pine wilt nematodes); *Hoplolaimus* spp. (lance nematodes); *Longidorus* spp. (needle nematodes); *Nacobbus* spp. (false root-knot nematodes); and *Aphelenchoides* spp. (foliar nematodes). The most efficient means for controlling nematodes is via nematicides that inhibit egg hatching, juvenile motility and/or plant infectivity. The development of chemical control for plant-parasitic nematodes is challenging because of both environmental and physiological reasons: (1) most phytoparasitic nematodes live in a confined area in soil near the roots and hence, delivery of a chemical nematicide is difficult and (2) the outer surface of nematodes is a poor biochemical target, and is impermeable to many organic molecules (Chitwood, D. J. (2003). Nematicides. Encyclopedia of Agrochemicals, vol 3. J. R. Plimmer. New York, John Wiley & Sons. 3: 1104-1115). Moreover, delivery of toxic compounds by an oral route is nearly impossible because most plant parasitic nematode species ingest material only after they have penetrated and infected plant roots. Therefore, nematicides have tended to be broad-spectrum toxins with high volatility or with other chemical and physical properties promoting their motility in soil.

According to Sasser and Freckman (In J. A. Veech and D. W. Dickson (Eds.), *Vistas on Nematology*, 1987, (pp. 7-14). Society of Nematologists, Hyattesville), crop losses by nematodes range from 8 to 20% on major crops around the world. Plant parasitic nematodes can cause considerable crop damage with annual losses estimated at $87 billion worldwide (Dong, L. Q. and Zhang, K. Q. (2006) *Plant Soil* 288:31-45). Fumigants such as methyl bromide are very effective in controlling both soil-borne plant diseases and nematodes but due to the high mammalian toxicity, ozone depleting effects and other residual effects, the use of methyl bromide has already been banned in various countries and its complete withdrawal from the market is planned by international agreement (Oka, Y., Nacar, S. et al. (2000). *Phytopathology* 90:710-715). Chemical alternatives such as methyl iodide, 1,3-Dichloropropene, and chloropicrin also have issues with mammalian and environmental safety. Chemical non-fumigant nematicides are being phased out and banned. Most recently, the US-EPA announced that aldicarb will be phased out.

Accordingly, there is currently a need for additional nematicides; in particular, those with maximal nematode-specific toxicity. In addition, in light of the ever-increasing resistance of plant pathogens to synthetic pesticides, and the environmental concerns associated with chemical pesticide use, there is a need for new, naturally-occurring pesticides (e.g., biopesticides) to which plant pathogens have not developed resistance, and which have minimal environmental effects.

SUMMARY

The present invention provides natural microbial pesticides for modulating infestation of a plant by plant parasitic nematodes.

In a particular embodiment, the present invention provides a method for modulating soybean cyst nematode (*H. glycines*) infestation of a plant comprising contacting the plant with an effective amount of a composition comprising *Flavobacterium* sp. H492 (NRRL Accession No. B-50584) to modulate the soybean cyst nematode infestation.

In another embodiment, the present invention provides a method for modulating soybean cyst nematode infestation of a plant comprising contacting the plant with an effective amount of composition comprising *Burkholderia* A396 (NRRL Accession No. B-50319) to modulate the soybean cyst nematode infestation.

In yet another embodiment, the present invention provides a method for modulating soybean cyst nematode infestation of a plant comprising contacting the plant with an effective amount of composition comprising *Chromobacterium subtsugae* sp. nov. (NRRL Accession No. B-30655) to modulate the soybean cyst nematode infestation.

In a particular embodiment, the composition of the invention is a whole cell broth, cell fraction, filtrate, supernatant, compound, and/or extract of the bacterial strain. In another embodiment, the composition is a formulation comprising the bacterial strain and inerts.

In certain embodiments, contacting the plant includes application of the composition to a seed of the plant prior to planting. In additional embodiments, contacting the plant is accomplished by adding the composition to the substrate in which the plant is grown (e.g., soil) either before, at the time of, or after planting the seed (e.g., by soil drenching or irrigation).

In an embodiment of the invention, the methods are capable of reducing the number of soybean cyst nematodes in the soil or plant, or on the plant, compared to a plant that not been contacted with the composition. Modulation can also include promotion of plant growth and/or increase in the yield of seeds produced by the plant, compared to a plant that has not been contacted with the composition.

In a particular embodiment of the invention, the plant is a soybean plant.

DETAILED DESCRIPTION

While the compositions and methods disclosed herein are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Definitions

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or medium used to culture or grow said organism.

As defined herein, "whole broth culture" or "whole cell broth" refers to a liquid culture containing both cells and media. A whole cell broth can also be obtained from bacteria grown on a plate, by harvesting the cells from the plate and suspending them in water or other liquid. The terms "whole broth culture" and "whole cell broth" are used interchangeably.

As defined herein, "supernatant" refers to the liquid remaining when cells grown in broth or harvested in another liquid from an agar plate and are removed by centrifugation, filtration, sedimentation, or other means well known in the art.

As defined herein, "filtrate" refers to liquid from a whole broth culture that has passed through a membrane.

As defined herein, "extract" refers to a liquid substance removed from cells by a solvent (water, detergent, buffer, organic solvent) and separated from the cells by centrifugation, filtration, phase partition or other method.

As defined herein, "metabolite" refers to a compound, substance or byproduct of fermentation of a microorganism, or supernatant, filtrate, or extract obtained from a microorganism that has pesticidal and particularly, nematicidal activity.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods and electrophoretic methods.

As defined herein, "carrier" is an inert, organic or inorganic material, with which the active ingredient is mixed or formulated to facilitate its application to a plant, seed or other object to be treated, or to facilitate its storage, transport and/or handling.

As defined herein, "modulate", is used to mean to alter the amount of pest infestation, plant growth, root extension, seed germination or rate of spread of pest infestation, rate of plant growth, rate of root extension, and/or rate of seed germination. Modulation includes reduction of pest infestation, increase in plant growth, increase in root extension, increase in seed germination, reduction of the rate of spread of pest infestation, increase in the rate of plant growth, increase in the rate of root extension, and/or increase in rate of seed germination.

As defined herein, "pest infestation" is the presence of a pest in an amount that causes a harmful effect including a disease or infection in a host population or emergence of an undesired pest in a growth system.

As defined herein, "pesticide" is a substance derived from a biological product or chemical substance that increase mortality or inhibit the growth rate of plant pests and includes but is not limited to nematicides, algaecides, herbicides, insecticides, plant fungicides, plant bactericides, and plant viricides.

As defined herein, a "plant parasitic nematode" is a nematode that feeds on and causes injury on any part of a plant.

As defined herein, "a non-parasitic nematode" is a nematode that exists independently in the soil and does not cause damage or injury to any part of a plant.

As defined herein, "substrate" is a surface or medium in which a plant grows. Substrate includes, but is not limited to, soil, an artificial growth surface or medium, water, and sediment.

*Chromobacterium*

A strain of *Chromobacterium* sp., particularly a strain of *Chromobacterium subtsugae* and more particularly, a strain of *Chromobacterium subtsugae* sp. nov. and even more particularly a strain of *Chromobacterium subtsugae* sp. nov. having the identifying characteristics of NRRL Accession No. B-30655, is described in U.S. Pat. No. 7,244,607. Methods of growing the *Chromobacterium* sp. and making a composition of *Chromobacterium* sp. and its products (e.g., a whole-cell broth) are described, for example, in U.S. Pub. No. 2012-0100236.

*Burkholderia*

A non-*Burkholderia cepacia* complex, non-*Burkholderia plantari*, non-*Burkholderia gladioli*, *Burkholderia* sp., in particular, *Burkholderia* A396 sp. nov. *rinojensis* (NRRL Accession No. B-50319), that is non-pathogenic to vertebrates, such as birds, mammals and fish, is described in, for example, U.S. Pub. No. 2011-0207604 and U.S. application Ser. No. 13/843,971. Methods of growing the *Burkholderia* sp. and making a composition of *Burkholderia* sp. and its products (e.g., a whole-cell broth) are also described in U.S. Pub. No. 2011-0207604 and U.S. application Ser. No. 13/843,971.

*Flavobacterium*

*Flavobacterium* sp., a gram negative bacterium, is a member of the Flavobacteriaceae family. In particular, the *Flavobacterium* species is *Flavobacterium* sp. H492 (NRRL Accession No. B-50584), as described in PCT App. No. PCT/US13/30631. Methods of growing the *Flavobacterium* sp. and making a composition of the *Flavobacterium* sp. and its products (e.g., a whole-cell broth) are also described in PCT App. No. PCT/US13/30631.

Compositions

Compositions comprise a strain from a *Chromobacterium* sp., *Burkholderia* sp., and/or *Flavobacterium* sp. The compositions may be a substantially pure culture, whole broth culture, liquid culture, suspension, cell fraction, supernatant, filtrate, extract, or compound of the bacterial strain, or combinations of the foregoing which in particular have nematicidal activity.

The compositions set forth above can be formulated in any manner. Non-limiting formulation examples include, but are not limited to, emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), seed treatments, etc. In any formulation described herein, percent of the active ingredient is within a range of about 0.01% to 99.99%.

The compositions may be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower. A composition may comprise gel-encapsulated active ingredient(s). Such gel-encapsulated materials can be prepared by mixing a gel-forming agent (e.g., gelatin, cellulose, or lignin) with a culture or suspension of live or inactivated bacterial strain of the present invention, or a cell-free filtrate or cell fraction of the bacterial culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) sorbitan monolaurate. The concentration of surfactants may range between about 0.1-35% of the total formulation; a preferred range is about 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may contain one or more of a *Chromobacterium* sp., *Burkholderia* sp., or *Flavobacterium* sp. and may be combined with another microorganism and/or pesticide (e.g., nematicide, fungicide, insecticide, herbicide). The microorganism may include, but is not limited to, an agent derived from *Bacillus* sp. (e.g., *B. firmus*, *B. thuringiensis*, *B. pumilus*, *B. licheniformis*, *B. amyloliquefaciens*, *B. subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp. (*S. bikiniensis*, *S. costaricanus*, *S. avermitilis*), *Trichoderma* sp., *Gliocladium* sp., avermectin, *Myrothecium* sp., *Paecilomyces* spp., *Sphingobacterium* sp., *Arthrobotrys* sp., *Chlorosplrnium* sp, *Neobulgaria* sp, *Daldinia* sp, *Aspergillus* sp, *Chaetomium* sp, *Lysobacter* sp, *Lachnum papyraceum*, *Verticillium suchlasporium*, *Arthrobotrys oligospora*, *Pochonia chlamydosporia* (synonym: *Verticillium chlamydosporium*), *Hirsutella minnesotensis*, *Hirsutella rhossiliensis*, *Pleurotus ostreatus*, *Omphalotus olearius*, *Lampteromyces japonicas*, *Brevudimonas* sp., and *Muscodor* sp.

The pesticide may be a natural oil, oil product or chemical pesticide. In particular, the agent may be a natural oil or oil-product having nematicidal, fungicidal and/or insecticidal activity (e.g., paraffinic oil, tea tree oil, lemongrass oil, clove oil, cinnamon oil, citrus oil (including but not limited to bitter orange, orange, lemon) rosemary oil, pyrethrum, allspice, bergamot, blue gum, camomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, and saponins.

The chemical pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a *Reynoutria* extract. The chemical pesticide can also be a multi-site non-inorganic, chemical fungicide. For example, the chemical fungicide may be chloronitrile, quinoxaline, sulphamide, phosphonate, phosphite, dithiocarbamate, chloralkythios, phenylpyridin-amine, or cyano-acetamide oxime.

Nematicides may include, but are not limited to, avermectin nematicides (e.g., abamectin); botanical nematicides (e.g., carvacrol); carbamate nematicides (e.g., benomyl carbofuran, carbosulfan, cloethocarb); oxime carbamate nematicides (e.g., alanycarb, aldicarb aldoxycarb, oxamyl tirpate); fumigant nematicides (e.g., carbon disulfide, cyanogen, 1,2-dichloropropane, 1,3-dichloropropene, dithioether, methyl bromide, methyl iodide, sodium tetrathiocarbonate); organophosphorus nematicides, which includes, but are not limited to, organophosphate nematicides (e.g., diamidafos, fenamiphos, fosthietan, phosphamidon); organothiophosphate nematicides (e.g., cadusafos, chlorpyrifos, dichlofenthion dimethoate ethoprophos, fensulfothion, fosthiazate, heterophos, isamidofos, isazofos, phorate, phosphocarb, terbufos, thionazin, triazophos); phosphonothioate nematicides (e.g., imicyafos, mecarphon); and other nematicides (e.g., acetoprole, benclothiaz, chloropicrin, dazomet, DBCP, DCIP, fluensulfone, furfural, metam, methyl isothiocyanate, xylenols, spirotetramat).

The compositions disclosed herein can also be used in combination with other growth promoting agents such as synthetic or organic fertilizers (e.g., di-ammonium phosphate in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and growth promoting microbes, such as *Bacillus* spp., Pseudomonads, Rhizobia, and *Trichoderma* spp.

Furthermore, the compositions can be used in combination with seed-coating agents. Such seed coating agents include, but are not limited to, ethylene glycol, carboxymethyl cellulose, methyl cellulose, polyethylene glycol, chitosan, carboxymethyl chitosan, peat moss, resins and waxes. The compositions may be applied using methods known in the art. Specifically, these compositions may be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plants include all parts and organs of plants above and below the ground, such as shoot, leaf, flower and root, examples which may be mentioned being leaves, needles, stalks, stems, flowers, fruit bodies, fruits, seeds, roots, tubers and rhizomes. The plants include, but are not limited to, harvested material, and vegetative and generative propagation material, for example cuttings, tubers, rhizomes, offshoots and seeds. Plants that may be treated include but are not limited to: (A) major edible food crops, which include but are not limited to (1) cereals (e.g., African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, *sorghum, Sorghum* spp., rye, spelt wheat); (2) fruits (e.g., abiu, acerola, achacha, African mangosteen, alpine currant, ambarella, American gooseberry, American persimmon, apple, apricot, arazá, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blue-berried honeysuckle, borojo, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee Arabica, coffee robusta, Costa Rica pitahaya, currants, custard apple, date, date-plum, dog rose, dragonfruit, durian, elderberry, elephant apple, Ethiopian eggplant, European nettle tree, European wild apple, feijoa, fig, gac, genipapo, giant granadilla, gooseberry, goumi, grape, grapefruit, great morinda, greengage, guava, hardy kiwi, hog plum, horned melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain papaya, mountain soursop, mulberry, naranjilla, natal plum, northern highbush blueberry, olive, otaheite gooseberry, oval kumquat, papaya, para guava, passionfruit, pawpaw, peach, peach-palm, pear, pepino, pineapple, pitomba *Eugenia luschnathiana*, pitomba *talisia esculenta*, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L. chinense*), yellow mombin, yellow pitaya, yellow-fruited strawberry, guava); (3) vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, barbados gooseberry, beet, beet root, bitter gourd, bitter vetch, bitterleaf, black mustard, black radish, black salsify, blanched celery, breadfruit, broad bean, broccoli, brussels sprout, Buck's horn plantain, buttercup squash, butternut squash, cabbage, caigua, calabash, caraway seeds, carob, carrot, cassabanana, cassava, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, good king henry, grass pea, groundut, guar bean, horse gram, horseradish, hyacinth bean, iceplant, Indian fig, Indian spinach, ivy gourd, Jerusalem artichoke, jicama, jute, kale, kohlrabi, konjac, kurrat, leek, lentil, lettuce, Lima bean, lotus, luffa, maca, maize, mangel-wurzel, mashua, moso bamboo, moth bean, mung bean, napa cabbage, neem, oca, okra, oldham's bamboo, olive, onion, parsnip, pea, pigeon pea, plantain, pointed gourd, potato, pumpkins, squashes, quinoa, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop *trapa bicornis*, water caltrop *trapa natans*, water morning slory, watercress, welsh onion, west African okra, west Indian gherkin, white goosefoot, white yam, winged bean, winter purslane, yacón, yam, yard-long bean, zucchinietables); (4) Food crops (e.g., abiu, acerola, achacha, ackee, African mangosteen, African rice, agate, air potato, alpine currant, *Amaranthus* app., Ambarrella, American gooseberry, American groundnut, American persimmon, antroewa, apple, apricot, arazá, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, betel nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blueberried honeysuckle, borojó, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassava, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (Arabica and Robusta types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, durum wheat, eddoe, eggplant, einkorn wheat, elderberry, elephant apple, elephant foot yam, elephant garlic, emmer wheat, endive, enset, Ethiopian eggplant, European nettle tree, European wild apple, feijoa, fig, finger millet, florence fennel, fluted gourd, foxtail millet, gac, garden rocket, garlic, genipapo, geocarpa groundnut, giant granadilla, good king henry, gooseberry, goumi, grape, grapefruit, grass pea, great morinda, greengage, groundnut, grumichama, guar bean, guava, hairy crabgrass, hardy kiwi, hog plum, horned melon, horse gram, horse mango, horseradish, hyacinth bean, iceplant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, luffa, lychee, maca, maize, malay apple, mamey saptoe, mammee apple, mangelwurzel, mango, mangosteen, maprang, marang, mashua, medlar, melon, Mirabelle plum, miracle fruit, monk fruit, monkey jack, moriche palm, moso bamboo, moth bean, mountain papaya, mountain soursop, mulberry, mung bean, mushrooms, nance, napa cabbage, naranjilla, natal plum, neem, northern highbush blueberry, oat, oca, oil palm, okra, oldman's bamboo, olive, onion, orange, otaheite gooseberry, oval kumquat, papaya, para guava, parsnip, passionfruit, pawpaw, pea, peach, peach-palm, pear, pearl millet, pepino, pigeon pea, pineapple, Pitomba (*Eugenia luschnathiana, Talisia esculenta*), plantain, plum, pointed gourd, pomegranate, pomelo, potato, proso millet, pulasan, pumpkins and squashes, purple chokeberry, quince, quinoa, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, *sorghum, Sorghum* spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, tef, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacón, yam, yangmei, yard-long bean, yellow mombin, yellow pitaya, yellow-fruited strawberry guava, zucchini; (B) Other edible crops, which includes but is not limited to (1) Herbs (e.g., Absinthium, alexanders, basil, bay laurel, betel nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, ginseng, gray santolina, herb hyssop, holy basil, hop, jasmine, kaffir lime, lavender, lemon balm, lemon basil, lemon grass, lovage, marjoram, mint, oregano, parsley, peppermint, perilla, pot marigold, rooibos, rosemary, sage, shiny-leaft buckthorn, sorrel, spearmint, summer savory, tarragon, Thai basil, valerian, watercress, wild betel, winter savory, yerba mate); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard);

(3) Medicinal plants (e.g., absinthium, alfalfa, aloe vera, anise, artichoke, basil, bay laurel, betel leaf, betel nut, bilberry, black cardamom, black mustard, black pepper, blue gum, borojó, camomlie, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray santolina, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red acacia, red currant, rooibos, safflower, sage, shiny-leaf buckthorn, sorrel, spilanthes, star anise, tarragon, tea, turmeric, valerian, velvet bean, watercress, white mustard, white sapote, wild betel, wolfberry (*Lycium barbarum, L. chinense*), yerba mate); (4) Stimulants (e.g., betel leaf, betel nut, cacao, chili pepper (*Capsicum annuum, C. baccatum, C. chinense, C. frutescens, C. pubescens*), chili peppers, coffee, coffee (Arabica, Robusta), cola nut, khat, Liberian coffee, tea, tobacco, wild betel, yerba mate); (5) Nuts (e.g., almond, betel nut, Brazil nut, cashew nut, chestnut, Chinese water chestnut, coconut, cola nut, common walnut, groundnut, hazelnut, Japanese stone oak, macadamia, nutmeg, paradise nut, pecan nut, pistachio nut, walnut); (6) Edible seeds (e.g., black pepper, Brazil nut, chilacayote, cola nut, fluted gourd, lotus, opium, quinoa, sesame, sunflower, water caltrop (*Trapa bicornis, T. natans*); (7) Vegetable oils (e.g., black mustard, camelina, castor bean, coconut, cotton, linseed, maize, neem, niger seed, oil palm, olive, opium, rapeseed, safflower, sesame, soybean, sunflower, tung tree, turnip); (8) Sugar crops (e.g., Asian palmyra palm, silver date palm, *sorghum*, sugar beet, sugarcane); (9) Pseudocereals (e.g., *Amaranthus* spp., buckwheat, quinoa, red amaranth); (10) Aphrodisiacs (e.g., borojó, celery, durian, garden rocket, ginseng, maca, red acacia, velvet bean); (C) Non food categories, including but not limited to (1) forage and dodder crops (e.g., agate, alfalfa, beet, broad bean, camelina, catjang, grass pea, guar bean, horse gram, Indian barnyard millet, Japanese barnyard millet, lespedeza, lupine, maize, mangel-wurzel, mulberry, niger seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassava, maize, rapeseed, *sorghum*, soybean, Sudan grass, sugar beet, sugarcane, wheat); (4) Alcohol production, (e.g., barley, plum, potato, sugarcane, wheat, *sorghum*); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray santolina, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, sunn hemp, trefoil, velvet bean, vetch); (7) Erosion prevention (e.g., bamboo, cocoplum); (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, chrysanthemum, daffodil, dahlia, freesia, gerbera, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, chrysanthemum, cocoplum, common lavender, crocus, daffodil, dahlia, freesia, gerbera, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia, almond, apple, apricot, arborvitae american, arborvitae nigra american, arborvitae, ash, aspen, azalea, baldcypress, beautybush, beech, birch, black tupelo, blackberry, blueberry, boxwood, buckeye, butterfly bush, butternut, camellia, catalpa, cedar, cherry, chestnut, coffeetree, crab trees, crabapple, crapemyrtle, cypress, dogwood, douglasfir, ebony, elder American, elm, fir, forsythia, ginkgo, goldenraintree, hackberry, hawthorn, hazelnut, hemlock, hickory, holly, honeylocust, horsechestnut, hydrangea, juniper, lilac, linden, magnolia, maple, mockorange, mountainash, oak, olive, peach, pear, pecan, pine, pistache, planetree, plum, poplar, pivet, raspberry, redbud, redcedar, redwood, rhododendron, rose-of-sharon, sassafras, sequoia, serviceberry, smoketree, soapberry, sourwood, spruce, strawberry tree, sweetshrub, sycamore, tuliptree, viburnum, walnut, weigela, willow, winterberry, witchhazel, zelkova; and (E) Turf, which includes, but is not limited to, Kentucky bluegrass, tall fescue, Bermuda grass, zoysia grass, perennial ryegrass, and fine fescues (e.g. creeping red, chewings, hard, or sheep fescue).

Methods of Production

*Chromobacterium* sp., *Burkholderia* sp., and/or *Flavobacterium* sp. may be cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media may be available from commercial sources or prepared according to published compositions.

After cultivation, a substantially pure culture or whole cell broth comprising said strain, or cell fraction, supernatant, filtrate, or compound (e.g., metabolite and/or extract) of or derived from said *Chromobacterium* sp., *Burkholderia* sp., and/or *Flavobacterium* sp. may be used in formulating a pesticidal composition. Alternatively, after cultivation, the compounds and/or metabolites may be extracted from the culture broth.

The extract may be fractionated by chromatography. Chromatographic fractions may be assayed for toxic activity against, for example, plant parasitic nematodes, such as *Heterodera glycines* (soybean cyst nematode), using methods known in the art. This process may be repeated one or more times using the same or different chromatographic methods.

Uses

The compositions, cultures, supernatants, metabolites and pesticidal compounds set forth above may be used as pesticides and in particular, may be used as nematicides, alone or in combination with one or more pesticidal substances set forth above and applied to plants, substrates for growing plants, or seeds as set forth herein.

Specifically, nematodes that may be controlled using the method set forth above include, but are not limited to, plant parasitic nematodes such as root-knot, reniform, cyst, and lesion nematodes, including but not limited to *Meloidogyne* sp., *Tylenchorhynchus* sp., *Belonolaimus* sp., *Hoplolaimus* sp., *Helicotylenchus* sp., *Pratylenchus* sp., *Rotylenchulus* sp., *Heterodera* sp. (e.g., *Heterodera glycines*), *Globodera* sp., *Trichodorus* sp., *Paratrichodorus* sp., *Xiphinema* sp., and *Criconema* sp. In particular, the plant parasitic nematodes may include but are not limited to seed gall nematodes (*Afrina wevelli*), bentgrass nematodes (*Anguina agrostis*), shoot gall nematodes (*Anguina* spp.), seed gall nematodes (*Anguina* spp., *A. amsinckiae, A. balsamophila; A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, spring crimp, strawberry foliar, strawberry nematodes, summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerae, Atalodera ucri*), spine nematodes (*Bakernema variabile*), sting nematodes (*Belonolaimus* spp., *B. gracilis, B. longicaudatus*), pine wood nematodes (*Bursaphalenchus* spp., *B. xylophilus, B. mucronatus*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stem and bulb nematodes (*Ditylenchus* spp., *D. angustus, D. dipsaci, D. destructor, D. intermedius*), Mushroom spawn nematodes (*D. myceliophagus*), awl nematodes (*Dolichodorus* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus, H. digonicus, H. dihystera, H. erythrinae, H. multicinctus, H. paragirus, H. pseudorobustus, H. solani, H. spicaudatus*), sheathoid nematodes (*Hemicriconemoides* spp., *H. biformis, H. californianus, H. chitwoodi, H. floridensis, H. wessoni*), sheath nematodes (*Hemicycliophora* spp., *H. arenaria, H. biosphaera, H. megalodiscus, H. parvana, H. poranga, H. sheri, H. similis, H. striatula*), cyst nematodes (*Heterodera* spp.), almond cyst nematodes (*H. amygdali*), oat (or cereal) cyst nematodes (*H. avenae*), Cajanus (or pigeon pea) cyst nematodes (*H. cajani*), Bermuda grass (or heart-shaped, or Valentine) cyst nematodes (*H. cardiolata*), carrot cyst nematodes (*H. carotae*), cabbage cyst nematodes or brassica root eelworm (*H. cruciferae*), nutgrass (or sedge) cyst nematodes (*H. cyperi*), Japanese cyst nematodes (*H. elachista*), fig (or ficus, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), rumex cyst nemtodes (*H. rumicis*), sugar beet cyst nematodes (*H. schachtii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli, H. caudacrena, H. gracilis, H. oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus, L. sylphus*), ring nematodes (*Macroposthonia* (*Mesocriconema xenoplax*), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens, M. conicus, M. grandis, M. microdorus*), root-knot nematodes (*Meloidogyne* spp., *M. acronea, M. arenaria, M. artiellia, M. brevicauda, M. camelliae, M. carolinensis, M. chitwoodi, M. exigua, M. graminicola, M. hapla, M. hispanica, M. incognita, M. incognita acrita, M. indica, M. inornata, M. javanica, M. kikuyuensis, M. konaensis, M. mali, M. microtyla, M. naasi, M. ovalis, M. platani, M. querciana, M. sasseri, M. tadshikistanica, M. thamesi*), knapweed nematodes (*Mesoanguina picridis*), Douglas fir nematodes (*Nacobbodera chitwoodi*), false root-knot nematodes (*Nacobbus aberrans, N. batatiformis, N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius, P. minor, P. porosus, P. reinter*), pin nematodes (*Paratylenchus* spp., *P. baldaccii, P. bukowinensis, P. curvitatus, P. dianthus, P. elachistus, P. hamatus, P. holdemani, P. italiensis, P. lepidus, P. nanus, P. neoamplycephalus, P. similis*), lesion (or meadow) nematodes (*Pratylenchus* spp., *P. alleni, P. brachyurus, P. coffeae, P. convallariae, P. crenatus, P. flakkensis, P. goodeyi, P. hexincisus, P. leiocephalus, P. minyus, P. musicola, P. neglectus, P. penetrans, P. pratensis, P. scribneri, P. thornei, P. vulnus, P. zeae*), stem gall nematodes (*Pterotylenchus cecidogenus*), grass cyst nematodes (*Punctodera punctate*), stunt nematodes (*Quinisulcius acutus, Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), *Sarisodera hydrophylla*, spiral nematodes (*Scutellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecavermiculatus andinus*), stubby-root nematodes (*Trichodorus* spp., *T. christiei, T kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T. ebriensis, T. elegans, T. golden, T graciliformis, T. martini, T. mashhoodi, T. microconus, T nudus, T. oleraceae, T. penniseti, T. punen-* sis), citrus nematodes (*Tylenchulus semipenetrans*), dagger nematodes (*Xiphinema* spp., *X. americanum*, *X. bakeri*, *X. brasiliense*, *X. brevicolle*, *X. chambersi*, *X. coxi*, *X. diversicaudatum*, *X. index*, *X. insigne*, *X. nigeriense*, *X. radicicola*, *X. setariae*, *X. vulgarae*, *X. vuittenezi*). In an even more particular embodiment, the nematodes, include but are not limited to *Meloidogyne incognita* (root knot nematodes), as well as *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode) and *Rotylenchulus reniformis* (reniform nematodes) (*Pratylenchus* spp.) (lesion nematodes), *Belonolaimus* sp. (sting nematode), *Hopolaimus* sp. (lance nematode), *Bursaphalenchus* spp., (e.g., pine wood nematodes), and *Ditylenchus* spp. (e.g., stem nematodes).

Application of an effective pesticidal controlling amount of a *Chromobacterium* sp., *Burkholderia* sp., and/or *Flavobacterium* sp. is provided. A substantially pure culture, whole cell broth, supernatant, filtrate, extract or compound of the bacterial strain may be applied, alone or in combination with another pesticidal substance, in an effective pest control or pesticidal amount. An "effective amount" is defined as the quantity of microorganism cells, supernatant, whole cell broth, filtrate, cell fraction or extract, metabolite and/or compound alone or in combination with another pesticidal substance that is sufficient to modulate plant parasitic nematode infestation. The amount that will be within an effective range can be determined by laboratory or field tests by those skilled in the art. In an embodiment of the invention, when the composition is applied directly to the seed, the effective amount is a concentration of about 0.01%-30% of the active ingredient (for example, the *Chromobacterium* sp., *Burkholderia* sp., or *Flavobacterium* sp.) per 100 g of seed. In another embodiment, the effective amount is a concentration of about 0.05%-25%, or about 0.1%-20%, or about 0.5%-15%, or about 1%-10%, or about 2%-5% of the active ingredient per 100 g of seed. In yet another embodiment, the effective amount is a concentration of about 0.5% to 1% of the active ingredient per 100 g of seed. In another embodiment of the invention, when the composition is applied to the soil by, for example, in furrow, the effective amount is about 0.1-50 oz of the active ingredient per 1000 ft row. In other embodiments, the effective amount for soil application is about 1-25 oz of the active ingredient per 1000 ft row. In yet another embodiment, the effective amount is about 2-20 oz, or about 3-15 oz, or about 4-10 oz, or about 5-8 oz, of the active ingredient per 1000 ft row.

The compositions, substantially pure culture, whole cell broth, supernatant, filtrate extract or compounds set forth above may modulate plant parasitic nematode infestation by a number of mechanisms. These include but are not limited to exterminating the plant parasitic nematodes at various stages of the life cycle (eggs, larvae or adult), affecting the motility of the plant parasitic nematodes, and/or reducing the number and/or viability of eggs that are laid by the parasitic nematodes.

The said formulated product can be used alone or sequentially with one or more other components as set forth above, such as growth promoting agents in a tank mix or in a program (sequential application called rotation) with predetermined order and application interval during the growing season.

Contact of the plants with the compositions set forth above may be carried out directly or by allowing the compositions to act on their surroundings, habitat or storage space by, for example, immersion, spraying, evaporation, fogging, scattering, painting on, injecting or soil amendment. In the case that the composition is applied to a seed, the composition may be applied to the seed as one or more coats prior to planting the seed using one or more coats using methods known in the art.

The compositions comprising a *Chromobacterium* sp., *Burkholderia* sp., and/or *Flavobacterium* sp. may be applied by root dip at transplanting, specifically by treating a fruit or vegetable with the composition by dipping roots of the fruit or vegetable in a suspension of said composition (about 0.25 to about 1.5% and more particularly about 0.5% to about 1.0% volume by volume) prior to transplanting the fruit or vegetable into the soil.

Alternatively, the composition may be applied by drip or other irrigation system. Specifically, the composition comprising a *Chromobacterium* sp., *Burkholderia* sp., and/or *Flavobacterium* sp. may be injected into a drip irrigation system. In a particular embodiment, the composition may be applied at a rate of about 11 to about 4 quarts per acre.

In yet another embodiment, the composition may be added as an in-furrow application. Specifically, the composition may be added as an in-furrow spray at planting using nozzles calibrated to deliver a total output of 2-6 gallons/acre, or at outputs of up to 20 gallons per acre. Nozzles are placed in the furrow opener on the planter so that the pesticide application and seed drop into the furrow are simultaneous. The mixtures set forth above and, where appropriate, a solid or liquid adjuvant are prepared in known manner. For example, the mixtures may be prepared by homogeneously mixing and/or grinding the active ingredients with extenders such as solvents, solid carriers and, where appropriate, surface-active compounds (surfactants). The compositions may also contain further ingredients such as stabilizers, viscosity regulators, binders, adjuvants as well as fertilizers or other active ingredients in order to obtain special effects.

NMR Spectroscopy Analysis of Compounds

NMR-NMR spectra were measured on a Bruker 600 Mhz gradient field spectrometer. The reference is set on the internal standard tetramethylsilane (TMS, 0.00 ppm). The amino acid analyses were carried out on Hitachi 8800 amino acid analyzer.

For structure elucidation, the purified chromamide A with molecular weight 860 is further analyzed using a 600 MHz NMR instrument, and has 1H NMR $\delta$ values at 8.89, 8.44, 8.24, 8.23, 7.96, 7.63, 6.66, 5.42, 5.36, 5.31, 5.10, 4.13, 4.07, 4.05, 3.96, 3.95, 3.88, 3.77, 3.73, 3.51, 3.44, 3.17, 2.40, 2.27, 2.11, 2.08, 2.03, 2.01, 1.97, 1.95, 1.90, 1.81, 1.68, 1.63, 1.57, 1.53, 1.48, 1.43, 1.35, 1.24, 1.07, 1.02, 0.96, 0.89, 0.88, 0.87, 0.80 (see FIG. 4) and has 13C NMR values of 173.62, 172.92, 172.25, 172.17, 171.66, 171.28, 170.45, 132.13, 130.04, 129.98, 129.69, 129.69, 125.48, 98.05, 70.11, 69.75, 68.30, 68.25, 64.34, 60.94, 54.54, 52.82, 49.72, 48.57, 45.68, 40.38, 39.90, 38.18, 36.60, 31.98, 31.62, 31.58, 29.53, 28.83, 27.78, 24.41, 23.06, 22.09, 20.56, 19.31, 18.78, 17.66, 15.80 (see FIG. 5). The chromamide A was isolated as a white solid, which analyzed for the molecular formula $C_{43}H_{68}N_6O_{12}$ (13 degrees of unsaturation), by ESI high-resolution mass spectrometry (obsd M+m/z 861.5376, calcd M+m/z 861.5343) (FIG. 3). The 1H NMR spectral data of chromamide A in DMSO-d6 exhibited 68 proton signals, in which nine protons [$\delta$H: 8.89, 8.44, 8.23, 8.22, 7.96, 7.64, 6.65, 5.10, 4.13], were assigned as either NH or OH due to lack of carbon correlation in a heteronuclear correlation NMR (HMQC) analysis. The 13C NMR spectrum, showed seven carbonyl signals [$\delta$c: 173.62, 172.92, 172.25, 1.72.17, 171.66, 171.28, 170.45] and in the 1H NMR spectrum, six characteristic α-amino protons signals [δH: 4.07, 4.06, 3.96, 3.95, 3.88, 3.72] were observed which demonstrate that chromamide A is a peptide.

EXAMPLE

The composition and methods set forth above will be further illustrated in the following, non-limiting Examples. The examples are illustrative of various embodiments only and do not limit the claimed invention regarding the materials, conditions, weight ratios, process parameters and the like recited herein.

A seed treatment trial was conducted to determine the effect of whole cell broths from *Flavobacterium* sp. H492 (MBI-302), *Chromobacterium subtsugae* sp. nov. (MBI-203), *Burkholderia* A396 (MBI-206), and enriched whole cell broth from *Flavobacterium* sp. H492 (MBI-302) on *Heterodera glycines* (soybean cyst nematode, SCN) infestation of soybean plants.

The study included six experimental seed treatments, an untreated control, and a standard (positive) control. Treatments of the seeds included the following:

1. Untreated control
2. Standard—AVICTA® Complete Soybean (Syngenta) 4.17 FS applied at 0.15 mg active ingredient per seed
3. *Flavobacterium* sp. H492 (MBI-302) @ 1 gram active ingredient per 100 grams seed
4. *Flavobacterium* sp. H492 (MBI-302) "enriched" @ 1 gram active ingredient per 100 grams seed
5. *Chromobacterium subtsugae* sp. nov. (MBI-203) @ 1 gram active ingredient per 100 grams seed
6. *Burkholderia* A396 (MBI-206) @0.5 gram active ingredient per 100 grams seed
7. *Burkholderia* A396 (MBI-206) @ 1.0 gram active ingredient per 100 grams seed
8. *Chromobacterium subtsugae* sp. nov. (MBI-203) in-furrow 5 oz per 1000 ft row in a minimum of 20 gallons per acre (GPA).

The term "enriched" (as used in treatment 4 above) refers to a MBI-302 whole-cell broth in which most of the water has been extracted to yield a concentrated cell paste.

Seed Treatment

Soybean seeds (94Y82) were prepared by weighing out the desired amount of seeds per treatment. Coating material, for application to seeds, consisted essentially of a sticking component (e.g. methyl cellulose) and whole cell broth from each of *Flavobacterium* sp. H492 (MBI-302), *Burkholderia* A396 (MBI-206), and *Chromobacterium subtsugae* sp. nov (MBI-203), enriched whole-cell broth from *Flavobacterium* sp. H492 (MBI-302) or AVICTA® Complete Soybean (Syngenta) (positive control). Negative control seeds were untreated. The amount of coating material was 2% of the weight of the seed. The coating material was applied to the seeds in a seed coater and the seeds were dried overnight.

Nematodes

*Heterodera glycines* were reared on Hutchinson soybeans for 60 days in a greenhouse, and inoculated into soil just prior to planting.

Planting and Plot Size

The trial was conducted in outdoor microplots (pots approximately 1 foot in diameter) having a volume of 19,000 $cm^3$, arranged in a randomized complete block design with 5 replicate plots for each of the eight treatments. Nematode-free field soil (Wickham fine sandy loam, 70-16-18 S-S-C, 1.0% OM, pH=6.5) was used. One week before planting, lime and fertilizer (OSMOCOAT® 10-10-10 Slow Release) (The Scotts Company) were added to the soil in each microplot and incorporated with a hand trowel. Lime was added to raise the pH of the soil to 7, which is optimal for soybean growth.

Soybean seeds, untreated or treated as described above, were planted in the pots in linear rows, at a density of ten seeds per foot. Immediately prior to planting, 500 cm3 of *H. glycines*-inoculated soil, containing at least 100 cysts, was mixed into each row. Plots were watered twice a day.

Data Recording

Seeds were planted on May 1, 2013. Fifty-seven days after planting (Jul. 30, 2013), plant height (distance from soil surface to plant top) was determined in three plants selected randomly from each plot. From these measurements, an average (mean) height was calculated. Mean plant heights for each of the eight treatments are shown in the third column of Table 1.

The number of cysts associated with each plant was also determined at fifty-seven days after planting. For measurement of cyst number, four core samples of 2.5×12 cm were obtained from each pot. The four samples were combined and homogenized, and 150 $cm^3$ of the homogenate was removed. Cysts were extracted from the 150 $cm^3$ sample by gravity screening on an 80 mesh sieve and counted. Results, expressed as mean cyst number, are shown in the fourth column of Table 1.

Seed production per plot was measured 127 days after planting (i.e., Oct. 8, 2013). All plants in a plot were cut down and placed in paper bags for three days for drying. Dried plants from each plot were hand-threshed, the seeds were collected and adjusted to 13% moisture content, then weighed. Results, expressed as mean seed weight per plot, are shown in the fifth column of Table 1.

TABLE 1

| Treatment | Concentration | Avg. Height | Cyst No. | Seed Wt. |
| --- | --- | --- | --- | --- |
| Untreated | — | 31.8 (a) | 35.9 (ab) | 84.2 (b) |
| AVICTA ® |  | 34.3 (a) | 13.8 (b) | 100.8 (ab) |
| MBI-302 | 1% | 33.9 (a) | 44.1 (a) | 91.3 (b) |
| MBI-302 enr | 1% | 33.9 (a) | 22.4 (ab) | 105.1 (ab) |
| MBI-203 | 1% | 35.6 (a) | 16.4 (ab) | 111.3 (ab) |
| MBI-206 | 0.5% | 34.7 (a) | 20.0 (ab) | 113.5 (ab) |
| MBI-206 | 1% | 33.9 (a) | 17.6 (ab) | 98.0 (a) |

TABLE 1-continued

| Treatment | Concentration | Avg. Height | Cyst No. | Seed Wt. |
|---|---|---|---|---|
| MBI-203 IF | 5 oz/$10^3$ ft. | 36.4 (a) | 17.0 (ab) | 136.8 (a) |
| | LSD | 3.589 | 0.259 | 42.72 |
| | Std. Dev. | 3.336 | 0.241 | 39.71 |
| | CV | 9.72 | 17.78 | 37.77 |

Test substances listed in the "Treatment" column included a commercial nematicide (AVICTA ®), whole-cell broths from *Flavobacterium* sp. H492 (MBI-302), *Chromobacterium subtsugae* sp. nov. (MBI-203), and *Burkholderia* A396 (MBI-206), and enriched whole cell broth from *Flavobacterium* sp. H492 (MBI-302 enr).
Test substances were coated onto seeds (soybean 94Y82), prior to planting, at the concentration (g/100 g seed) shown in the "Conc." column, except for MBI-203 IF which was applied to soil just prior to planting at a concentration of 5 oz per 1000 ft in a minimum of 20 gallons per acre.
Heights are expressed in cm; seed weights are expressed in grams per plot.
Mean values followed by the same letter do not significantly differ (p = 0.1, Student-Newman-Kuels test)
LSD: Least significant difference at 90% confidence level (p = 0.1)
Std. Dev.: Standard deviation
CV: Coefficient of Variation Data Analysis Least significant difference (Fisher's LSD) values were obtained for plant height, cyst number and seed weight values, as shown in Table 1. Values that differ from the control untreated value by more than the LSD indicate that the difference in values has a 90% probability of resulting from the treatment. By this criterion, both seed coating with, and in-furrow application of, MBI-203 reverse the growth inhibition caused by SCN infestation; and both performed better than the commercial nematicide (Table 1, Column 3).

With respect to cyst number, whole-cell broth from MBI-203 and MBI-206, and enriched whole-cell broth from MBI-302 all reduced the number of cysts associated with infested plants (Table 1, Column 4).

Finally, in-furrow application of MBI-203 increased the amount of seed produced by SCN-infested plants (Table 1, Column 5).

These results show that application of MBI-203, MBI-206 and/or MBI-302 to seeds or soil is effective in reducing the number of SCN cysts in the soil, after seeds are planted in SCN-infested soil. They also show that MBI-203 reduces growth inhibition caused by SCN infestation, and increases seed yield in SCN-infested soybean plants. They also show that MBI-302 and MBI-206 treated plots are not different from the commercial nematicide in yields per plot.

This invention may be embodied in other forms or carried out in other ways without departing from the spirit or essential characteristics thereof. The present disclosure is therefore to be considered as in all aspects illustrate and not restrictive, and all changes which come within the meaning and range of equivalency are intended to be embraced therein.

Various references are cited throughout this specification, each of which is incorporated herein by reference in its entirety.

What is claimed is:

1. A method for modulating soybean cyst nematode infestation of a plant comprising the steps of:

contacting the plant, one or more seeds of the plant, and/or soil in which the plant is grown, with a composition comprising a fermented whole cell broth collected from a bacterial strain of *Flavobacterium* sp. H492 (NRRL Accession No. B-50584), in an amount effective to modulate the soybean cyst nematode infestation.

2. The method of claim 1, wherein the contacting comprises applying the composition to one or more seeds of the plant prior to planting.

3. The method of claim 1, wherein the contacting comprises adding the composition to a soil in which the plant is grown.

4. The method of claim 3, wherein the composition is added to the soil by in furrow irrigation.

5. The method of claim 1, wherein the method reduces the number of soybean cyst nematodes in the soil, in the plant, or on the plant, compared to a plant that has not been contacted with the composition.

6. The method of claim 1, wherein the method promotes growth of the plant or the one or more seeds of the plant, compared to a plant that has not been contacted with the composition.

7. The method of claim 1, wherein the method increases the yield of one or more seeds produced by the plant, compared to a plant that has not been contacted with the composition.

8. The method of claim 1, wherein the plant is a soybean plant.

* * * * *